United States Patent
Ebert et al.

(10) Patent No.: US 9,974,985 B2
(45) Date of Patent: *May 22, 2018

(54) ETHERAMINES BASED ON 1,2-DIALCOHOLS

(71) Applicant: BASF SE, Ludwigshafen (DE)

(72) Inventors: Sophia Ebert, Mannheim (DE); Björn Ludolph, Ludwigshafen (DE); Christof Wilhelm Wigbers, Mannheim (DE); Dieter Boeckh, Limburgerhof (DE); Frank Huelskoetter, Bad Dürkheim (DE); Stefano Scialla, Rome (IT); Kevin Christmas, Mason, OH (US); Darren Rees, Newcastle upon Tyne (GB); Brian J. Loughnane, Sharonville, OH (US)

(73) Assignee: BASF SE, Ludwigshafen am Rhein (DE)

( * ) Notice: Subject to any disclaimer, the term of this patent is extended or adjusted under 35 U.S.C. 154(b) by 9 days.

This patent is subject to a terminal disclaimer.

(21) Appl. No.: 14/710,845

(22) Filed: May 13, 2015

(65) Prior Publication Data

US 2015/0329476 A1 Nov. 19, 2015

Related U.S. Application Data

(60) Provisional application No. 61/993,316, filed on May 15, 2014.

(51) Int. Cl.

| | |
|---|---|
| *C11D 3/32* | (2006.01) |
| *C11D 3/37* | (2006.01) |
| *C11D 7/32* | (2006.01) |
| *A61Q 19/10* | (2006.01) |
| *C07C 217/46* | (2006.01) |
| *A61K 8/41* | (2006.01) |
| *C11D 3/30* | (2006.01) |
| *A61Q 5/02* | (2006.01) |
| *C07C 213/04* | (2006.01) |
| *A61K 8/45* | (2006.01) |

(52) U.S. Cl.
CPC .............. *A61Q 19/10* (2013.01); *A61K 8/41* (2013.01); *A61K 8/45* (2013.01); *A61Q 5/02* (2013.01); *C07C 213/04* (2013.01); *C07C 217/46* (2013.01); *C11D 3/30* (2013.01); *C11D 3/3723* (2013.01)

(58) Field of Classification Search
CPC .............................. C11D 3/3723; C11D 3/30
USPC ........ 510/119, 136, 137, 138, 499, 505, 506
See application file for complete search history.

(56) References Cited

U.S. PATENT DOCUMENTS

| | | |
|---|---|---|
| 2,654,370 A | 10/1953 | Smith |
| 3,151,112 A | 9/1964 | Moss |
| 3,654,370 A | 4/1972 | Yeakey |
| 5,530,127 A | 6/1996 | Reif et al. |
| 6,347,055 B1 | 2/2002 | Motomura |

(Continued)

FOREIGN PATENT DOCUMENTS

| | | | |
|---|---|---|---|
| EP | 696572 A1 | | 2/1996 |
| WO | WO97/30103 | * | 8/1997 |
| WO | WO-2004/0020506 A2 | | 3/2004 |
| WO | WO-09138387 A1 | | 11/2009 |
| WO | WO-09153193 A1 | | 12/2009 |
| WO | WO-10010075 A1 | | 1/2010 |
| WO | WO-10026030 A1 | | 3/2010 |
| WO | WO-2010026066 A1 | | 3/2010 |
| WO | WO-2011/067199 A1 | | 6/2011 |
| WO | WO-2011/067200 A1 | | 6/2011 |

OTHER PUBLICATIONS

Chinese Office Action with English Translation for Chinese Application No. 201580016191.3, dated Jul. 3, 2017.

(Continued)

*Primary Examiner* — Gregory R Delcotto
(74) *Attorney, Agent, or Firm* — Drinker Biddle & Reath LLP

(57) ABSTRACT

The invention relates to etheramines of formula (I) or formula (II) or a mixture of etheramines of formula (I) and formula (II) based on 1,2-dialcohols, wherein $R_1$ is a linear or branched alkyl group with 2 to 16 carbon atoms, $R_2$ is a hydrogen or an alkyl group with 1 to 16 carbon atoms, $x \geq 1$ and $y \geq 1$ and the sum of $x+y$ is between 2 and 10, and $A_1$, $A_2$, $A_3$ and $A_4$ are independently selected from the group consisting of linear and/or branched alkylenes having 2 to 18 carbon atoms and wherein $Z_1$-$Z_4$ are independently selected from OH, $NH_2$, NHR' or NR'R", wherein at least one of $Z_1$-$Z_2$ and at least one of $Z_3$-$Z_4$ is $NH_2$, NHR' or NR'R", wherein R' and R" are independently selected from alkylenes having 2 to 6 carbon atoms.

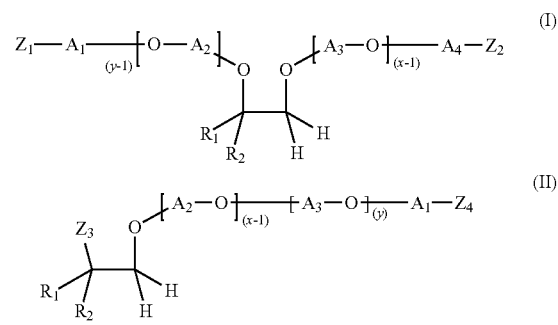

The invention further relates to etheramines obtainable by the alkoxylation and amination of 1,2-dialcohols.

24 Claims, No Drawings

(56) References Cited

U.S. PATENT DOCUMENTS

| | | |
|---|---|---|
| 8,318,982 B2 | 11/2012 | Kubanek et al. |
| 8,487,135 B2 | 7/2013 | Kubanek et al. |
| 8,519,084 B2 | 8/2013 | Mijolovic et al. |
| 8,530,570 B2 | 9/2013 | Mijolovic et al. |
| 2011/0040030 A1 | 2/2011 | Mijolovic et al. |
| 2011/0144259 A1 | 6/2011 | Mijolovic et al. |
| 2011/0178239 A1 | 7/2011 | Mijolovic et al. |
| 2012/0065362 A1* | 3/2012 | Amey ................ C08G 65/3255 528/407 |
| 2015/0275142 A1* | 10/2015 | Hulskotter ........... C11D 3/3723 510/320 |

OTHER PUBLICATIONS

Rist, et al., "Synthesis of Novel Diammonium Gemini Surfactants", Molecules, 2001, vol. 6, pp. 979-987.

* cited by examiner

ETHERAMINES BASED ON 1,2-DIALCOHOLS

CROSS-REFERENCE TO RELATED APPLICATIONS

This application claims priority to U.S. Application No. 61/993,316, filed May 15, 2014, which is incorporated herein by reference in its entirety.

This Patent is subject to a Joint Research and Development Agreement pursuant to 35 U.S.C. § 102(c)(3). The names of the Parties to the Joint Research and Development Agreement are as follows:
a. BASF SE, Ludwigshafen, Germany;
b. Procter & Gamble Co., Cincinnati, Ohio, United States of America.

This invention relates to etheramines based on 1,2-dialcohols, in particular to etheramines obtainable by the alkoxylation and amination of 1,2-dialcohols.

Due to the increasing popularity of easy-care fabrics made of synthetic fibers as well as the ever increasing energy costs and growing ecological concerns of detergent users, the once popular hot water wash has now taken a back seat to washing fabrics in cold water. Many commercially available laundry detergents are even advertised as being suitable for washing fabrics at 40° C. or 30° C. or even at room temperature. To achieve satisfactory washing result at such low temperatures, results comparable to those obtained with hot water washes, the demands on low-temperature detergents are especially high.

It is known to include certain additives in detergent compositions to enhance the detergent power of conventional surfactants so as to improve the removal of grease stains at temperatures of 60° C. and below.

WO 2004/020506 A2 discloses polyamine compositions prepared via alkoxylation of starting materials which may consist of 1,2-glycols, such as ethylene glycol and propylene glycol or higher diols such as diethylene glycol or dipropylene glycol. The polyol thus obtained may be aminated. Such polyamine precursors are useful in the manufacture of epoxy resins.

U.S. Pat. No. 6,347,055 B1 reads on curable coating compositions comprising a polyoxyalkylene polyamine containing a repetitive dialcohol core unit.

Additionally, U.S. Pat. No. 3,654,370 describes polyoxyalkylene polyamine prepared by the addition of ethylene oxide, propylene oxide or mixtures thereof to ethylene glycol, propylene glycol, glycerine or trimethyloipropane.

DETAILED DESCRIPTION OF THE INVENTION

There is a continuous need for cleaning compositions that remove grease stains from fabrics and other soiled materials, as grease stains are challenging stains to remove. Conventional cleaning compositions directed to grease removal frequently utilize various amine compounds which tend to show strong negative impacts on whiteness. As a consequence there is still a continual need for improved amine compositions which provide improved grease removal from fabrics and other soiled materials and at the same time do not negatively impact the clay cleaning.

It was an object of the present invention to provide compounds which would improve the washing performance of detergents at low temperatures, i.e. at temperatures as low as 30° C. or even lower.

This goal was achieved with an etheramine of formula (I) or formula (II),

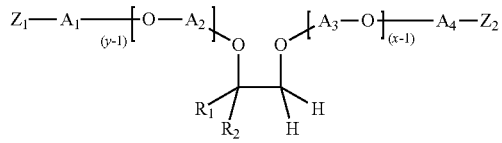
Formula (I)

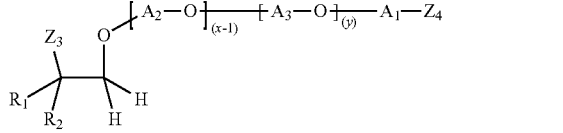
Formula (II)

or a mixture of etheramines of formula (I) and formula (II), wherein
$R_1$ is a linear or branched alkyl group with 2 to 16 carbon atoms,
$R_2$ is a hydrogen or an alkyl group with 1 to 16 carbon atoms,
$x \geq 1$ and $y \geq 1$ and the sum of x+y is between 2 and 10, and
$A_1, A_2, A_3$ and $A_4$ are independently selected from the group consisting of linear and/or branched alkylenes having 2 to 18 carbon atoms,
wherein $Z_1$-$Z_4$ are independently selected from OH, $NH_2$, NHR' or NR'R", wherein at least one of $Z_1$-$Z_2$ and at least one of $Z_3$-$Z_4$ is $NH_2$, NHR' or NR'R", wherein R' and R" are independently selected from alkylenes having 2 to 6 carbon atoms.

Preferably $A_1, A_2, A_3$ and $A_4$ are independently selected from 1,2-propylene and 1,2-butylene, more preferably $A_1, A_2, A_3$ and $A_4$ are independently selected from 1,2-propylene and 1,2-butylene and at least one of $A_1, A_2, A_3$ or $A_4$ is 1,2-propylene, even more preferably $A_1, A_2, A_3$ and $A_4$ are 1,2-propylene.

Preferably, the sum of x and y is in the range of from 3 to 8, more preferably in the range of from 4 to 6.

In a preferred embodiment, $R_1$ is a linear or branched alkyl group with 3 to 16 carbon atoms and $R_2$ is a hydrogen or an alkyl group with 1 to 16 carbon atoms. In another preferred embodiment, $R_1$ is a linear alkyl group with 3 to 8 carbon atoms and $R_2$ is a hydrogen.

Preferably all groups $Z_1, Z_2, Z_3$ and $Z_4$ are $NH_2$.

The etheramine of formula (I) or formula (II) has a weight average molecular weight of about 270 to about 1000 grams/mole, preferably of from about 270 to about 650 grams/mole.

The etheramine of formula (I) or formula (II) is obtainable by a process comprising the following steps:
a) the alkoxylation of a 1,2-dialcohol of formula (III) with $C_2$-$C_{18}$ alkylene oxides, wherein the molar ratio of the 1,2-dialcohol of formula (III) to $C_2$-$C_{18}$ alkylene oxides is in the range of 1:2 to 1:10,

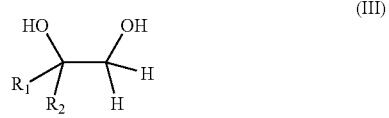
(III)

wherein $R_1$ is a linear or branched alkyl group with 3 to 16 carbon atoms and $R_2$ is a hydrogen or an alkyl group with 1 to 16 carbon atoms, b) aminating the alkoxylated 1,2-diol with ammonia.

In a preferred embodiment the molar ratio of 1,2-diol to $C_2$-$C_{18}$ alkylene oxides is in the range of 1:3 to 1:8, even more preferably in the range of 1:4 to 1:6.

Preferably the $C_2$-$C_{18}$ alkylene oxides are selected from the group consisting of propylene oxide, butylene oxide or a mixture thereof, even more preferably $C_2$-$C_{18}$ alkylene oxide is propylene oxide.

Preferably in the 1,2-diol of formula (III) is selected from the group consisting of 1,2-pentanediol, 1,2-hexanediol, 1,2-heptanediol, 1,2-octanediol, 1,2-nonanediol, 1,2-decanediol and 1,2-dodecanediol, 1,2-tetradecandiol, 1,2 hexadecandiol and 1,2 octadecandiol.

Step a): Alkoxylation

Substituted 1,2 diols (formula III) are synthesized according to WO10026030, WO10026066, WO09138387, WO09153193, WO10010075.

Alkoxylated 1,2-diols are obtained by reaction of 1,2-diols (formula Ill) with alkylene oxides and can be affected according to general alkoxylation procedures known in the art.

The alkoxylated 1,2-diols may be prepared in a known manner by reaction of 1,2-diols with alkylene oxides. Suitable alkylene oxides are $C_2$-$C_{18}$ alkylene oxides like ethylene oxide, propylene oxide, butylene oxide, pentene oxide, hexene oxide, decene oxide, dodecene oxide etc.

Preferably $C_2$-$C_{18}$ alkylene oxides are propylene oxide, butylene oxide or a mixture thereof, even more preferably $C_2$-$C_{18}$ alkylene oxides are propylene oxide.

The 1,2-diols are reacted with one single alkylene oxide or combinations of two or more different alkylene oxides. Using two or more different alkylene oxides, the resulting polymer can be obtained as a block-wise structure or a random structure.

The molar ratio of molar ratio of 1,2-diol to $C_2$-$C_{18}$ alkylene oxides at which the alkoxylation reaction is carried out lies in the range of 1:2 to 1:10, preferably in the range of 1:3 to 1:8, even more preferably in the range of 1:4 to 1:6.

This reaction is undertaken generally in the presence of a catalyst in an aqueous solution at a reaction temperature from about 70 to about 200° C. and preferably from about 80 to about 160° C. This reaction may be affected at a pressure of up to about 10 bar, and in particular up to about 8 bar.

Examples of suitable catalysts are basic catalysts such as alkali metal and alkaline earth metal hydroxides such as sodium hydroxide, potassium hydroxide and calcium hydroxide, alkali metal alkoxides, in particular sodium and potassium $C_1$-$C_4$-alkoxides, such as sodium methoxide, sodium ethoxide and potassium tert-butoxide, alkali metal and alkaline earth metal hydrides such as sodium hydride and calcium hydride, and alkali metal carbonates such as sodium carbonate and potassium carbonate. Preference is given to alkali metal hydroxides, particular preference being given to potassium hydroxide and sodium hydroxide. Typical use amounts for the base are from 0.05 to 10% by weight, in particular from 0.1 to 2% by weight, based on the total amount of polyalkyleneimine and alkylene oxide.

Alkoxylation with x+y $C_2$-$C_{18}$ alkylene oxides leads to structures as drawn in formula IV and/or formula V

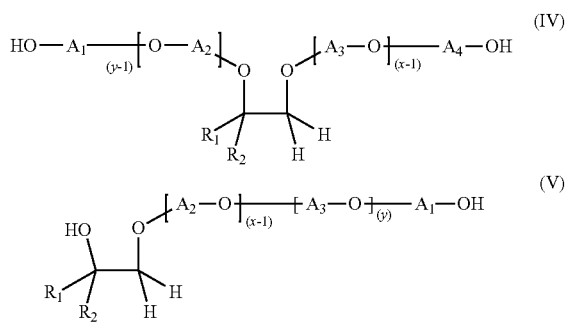

$R_1$ is a linear or branched alkyl group with 3 to 16 carbon atoms, $R_2$ is a hydrogen or an alkyl group with 1 to 16 carbon atoms, $x \geq 1$ and $y \geq 1$ and the sum of x+y is between 2 and 10, and $A_1, A_2, A_3$ and $A_4$ are independently selected from the group consisting of linear and/or branched alkylenes having 2 to 18 carbon atoms.

Step b): Amination

Amination of the alkoxylated 1,2-dialcohols leads to structures with formula (I) or formula (II):

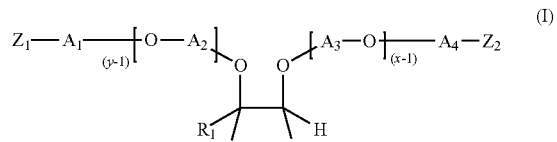

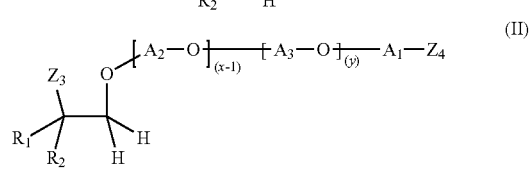

wherein $R_1$ is a linear or branched alkyl group with 3 to 16 carbon atoms, $R_2$ is a hydrogen or an alkyl group with 1 to 16 carbon atoms, $x \geq 1$ and $y \geq 0.1$ and the sum of x+y is between 2 and 10, and $A_1, A_2, A_3$ and $A_4$ are independently selected from the group consisting of linear and/or branched alkylenes having 2 to 18 carbon atoms and wherein $Z_1$-$Z_4$ are independently selected from OH, $NH_2$, NHR' or NR'R", wherein at least one of $Z_1$-$Z_2$ and at least one of $Z_3$-$Z_4$ is $NH_2$, NHR' or NR'R", wherein R' and R" are independently selected from alkylenes having 2 to 6 carbon atoms.

Etheramines of formula (I) or formula (II) or a mixture of etheramines of formula (I) and formula (II) are obtained by reductive amination of the alkoxylated 1,2-dialcohols of formula (IV) or formula (V) with ammonia in presence of hydrogen and a catalyst containing nickel. Suitable catalysts are described in WO 2011/067199 A1 and in WO2011/067200 A1, and in EP0696572 B1. Preferred catalysts are supported copper-, nickel- and cobalt-containing catalysts, wherein the catalytically active material of the catalysts, before the reduction thereof with hydrogen, comprises oxygen compounds of aluminium, of copper, of nickel and of cobalt, and in the range from 0.2 to 5.0% by weight of oxygen compounds of tin, calculated as SnO. Other preferred catalysts are supported copper-, nickel- and cobalt-containing catalysts, wherein the catalytically active material of the catalysts, before the reduction thereof with hydrogen, comprises oxygen compounds of aluminium, of copper, of nickel, of cobalt and of tin, and in the range from 0.2 to 5.0% by weight of oxygen compounds of yttrium, of lanthanum, of cerium and/or of hafnium, each calculated as $Y_2O_3$, $La_2O_3$, $Ce_2O_3$ and $Hf_2O_3$ respectively. Another preferred catalyst is a zirconium, copper, nickel catalyst, wherein the catalytically active composition comprises from 20 to 85% by weight of oxygen-containing zirconium compounds, calculated as $ZrO_2$, from 1 to 30% by weight of oxygen-containing compounds of copper, calculated as CuO, from 30 to 70% by weight of oxygen-containing compounds of nickel, calculated as NiO, from 0.1 to 5% by weight of oxygen-containing compounds of aluminium and/or manganese, calculated as Al2O3 and MnO2 respectively.

For the reductive amination step as well supported as non-supported catalyst can be used. The supported catalyst is obtained by deposition of the metallic components of the catalyst compositions onto support materials known to those skilled in the art, using techniques which are well-known in the art including without limitation, known forms of alumina, silica, charcoal, carbon, graphite, clays, mordenites; and molecular sieves, to provide supported catalysts as well. When the catalyst is supported, the support particles of the catalyst may have any geometric shape, for example the shape of spheres, tablets or cylinders in a regular or irregular version.

The process can be carried out in a continuous or discontinuous mode, e.g. in an autoclave, tube reactor or fixed-bed reactor. The reactor design is also not narrowly critical. The feed thereto may be upflowing or downflowing, and design features in the reactor which optimize plug flow in the reactor may be employed.

By-products which contain secondary or tertiary amino functions may be formed under amination reaction conditions. Secondary amines are e.g. obtained from a reaction of a fully or partially aminated diol with another fully and/or partially aminated diol. Tertiary amines are formed e.g. via a reaction of a secondary amine with another fully or partially aminated diol.

The degree of amination is between 50 to 100%, preferably from 75% to 100% and most preferably from 90 to 100%.

The degree of amination is calculated from the total amine value (AZ) divided by sum of the total acetylables value (AC) and tertiary amine value (tert. AZ) multiplicated by 100: (Total AZ: (AC+tert. AZ)×100).

The total amine value (AZ) is determined according to DIN 16945.

The total acetylables value (AC) is determined according to DIN 53240.

The secondary and tertiary amine are determined according to ASTM D2074-07.

The hydroxyl value is calculated from (total acetylables value+tertiary amine value)−total amine value.

The etheramines of the invention can also be used for cleaning compositions in form of a solution or emulsion of the etheramine in water together with an acid like for example citric acid, lactic acid, sulfuric acid, methanesulfonic acid, aqueous hydrogen chloride or phosphoric acid. The preferred pH of the solution or emulsion ranges from pH 6 to pH 9.5, even more preferred from pH 7 to pH 8.5.

In another preferred embodiment, the etheramines of the invention can also be further reacted with an acid. The acid may be selected from the group consisting of citric acid, lactic acid, sulfuric acid, methanesulfonic acid, hydrogen chloride, phosphoric acid, formic acid, acetic acid, propionic acid, valeric acid, oxalic acid, succinic acid, adipic acid, sebacic acid, glutaric acid, glucaric acid, tartaric acid, malic acid, benzoic acid, salicylic acid, phthalic acid, oleic acid, stearic acid and mixtures thereof. In an alternative embodiment, the etheramines of the invention may, in protonated form, have a surfactant as a counter ion, as obtained from e.g. linear alkyl benzene sulphonic acid.

Alternatively, dialky-substituted tertiary polyether amines can be obtained by reacting a polyether alcohol with a dialkylamine like e.g. dimethylamine in the presence of a suitable transition metal catalyst, and preferably in the additional presence of hydrogen and under continuous removal of the reaction water.

Applications

The inventive etheramine mixtures may be used used in personal care, especially in shampoo and body wash formulations.

They may also be used as curing agent for epoxy resins or as a reactant in the production of polymers but also in polyurethanes, polyureas, epoxy resins, polyamides.

The inventive polyetheramines have proved to be effective for removal of stains, particularly grease, from soiled material. Besides, cleaning compositions with inventive polyetheramines also do not have the cleaning negatives seen with conventional, amine cleaning compositions for hydrophilic bleachable stains, such as coffee, tea, wine, or particulates. Additionally, for stain removal from white fabric, cleaning compositions with inventive polyetheramines do not cause the whiteness negatives that commercially available, amine cleaning compositions cause.

A further advantage of cleaning compositions comprising the inventive etheramines is their ability to remove grease stains in cold water cleaning solutions, via pretreatment of the grease stain outside the washing machine, followed by cold water washing. Without being limited by theory, cold water solutions have the effect of causing greases to harden or solidify, making greases more resistant to removal, especially from fabric. Cleaning compositions with an etheramine of formula (I) or formula (II) or a mixture of etheramines of formula (I) and formula (II) however, are surprisingly effective when used in pretreatment followed by cold water cleaning.

As used herein the phrase "cleaning composition" includes compositions and formulations designed for cleaning soiled material. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, liquid hand dishwashing composition, detergent contained on or in a porous substrate or nonwoven sheet, automatic dishwashing agent, hard surface cleaner, and other suitable forms that may be apparent to one skilled in the art in view of the teachings herein. Such compositions may be used as a pre-laundering treatment, a post-laundering treatment, may be added during the rinse or wash cycle of the laundering operation, or used in homecare cleaning applications. The cleaning compositions may have a form selected from liquid, powder, single-phase or multi-phase unit dose, pouch, tablet, gel, paste, bar, or flake.

The cleaning compositions described herein may include from about 0.1% to about 10%, in some examples, from about 0.2% to about 5%, and in other examples, from about 0.5% to about 3%, by weight the composition, of an etheramine of formula (I) or formula (II) or a mixture of etheramines of formula (I) and formula (II).

The inventive etheramine mixtures are effective for removal of stains, particularly grease, from soiled material. Cleaning compositions containing the amine-terminated polyalkylene glycols of the invention also do not exhibit the cleaning negatives seen with conventional amine-containing cleaning compositions on hydrophilic bleachable stains, such as coffee, tea, wine, or particulates. Additionally, unlike conventional amine-containing cleaning compositions, the amine-terminated polyalkylene glycols of the invention do not contribute to whiteness negatives on white fabrics.

A further advantage of cleaning compositions containing the inventive etheramine mixture is their ability to remove grease stains in cold water, for example, via pretreatment of a grease stain followed by cold water washing. Without being limited by theory, it is believed that cold water washing solutions have the effect of hardening or solidifying grease, making the grease more resistant to removal, especially on fabric. Cleaning compositions containing the etheramines of the invention are surprisingly effective when used as part of a pretreatment regimen followed by cold water washing.

Surfactant System

The cleaning compositions comprise a surfactant system in an amount sufficient to provide desired cleaning properties. In some embodiments, the cleaning composition comprises, by weight of the composition, from about 1% to about 70% of a surfactant system. In other embodiments, the liquid cleaning composition comprises, by weight of the composition, from about 2% to about 60% of the surfactant system. In further embodiments, the cleaning composition comprises, by weight of the composition, from about 5% to about 30% of the surfactant system. The surfactant system may comprise a detersive surfactant selected from anionic surfactants, nonionic surfactants, cationic surfactants, zwitterionic surfactants, amphoteric surfactants, ampholytic surfactants, and mixtures thereof. Those of ordinary skill in the art will understand that a detersive surfactant encompasses any surfactant or mixture of surfactants that provide cleaning, stain removing, or laundering benefit to soiled material.

Adjunct Cleaning Additives

The cleaning compositions of the invention may also contain adjunct cleaning additives. Suitable adjunct cleaning additives include builders, structurants or thickeners, clay soil removal/antiredeposition agents, polymeric soil release agents, polymeric dispersing agents, polymeric grease cleaning agents, enzymes, enzyme stabilizing systems, bleaching compounds, bleaching agents, bleach activators, bleach catalysts, brighteners, dyes, hueing agents, dye transfer inhibiting agents, chelating agents, suds supressors, softeners, and perfumes.

Methods of Use

The present invention includes methods for cleaning soiled material. As will be appreciated by one skilled in the art, the cleaning compositions of the present invention are suited for use in laundry pretreatment applications, laundry cleaning applications, and home care applications.

Such methods include, but are not limited to, the steps of contacting cleaning compositions in neat form or diluted in wash liquor, with at least a portion of a soiled material and then optionally rinsing the soiled material. The soiled material may be subjected to a washing step prior to the optional rinsing step.

For use in laundry pretreatment applications, the method may include contacting the cleaning compositions described herein with soiled fabric. Following pretreatment, the soiled fabric may be laundered in a washing machine or otherwise rinsed.

Machine laundry methods may comprise treating soiled laundry with an aqueous wash solution in a washing machine having dissolved or dispensed therein an effective amount of a machine laundry cleaning composition in accord with the invention. An "effective amount" of the cleaning composition means from about 20 g to about 300 g of product dissolved or dispersed in a wash solution of volume from about 5 L to about 65 L. The water temperatures may range from about 5° C. to about 100° C. The water to soiled material (e.g., fabric) ratio may be from about 1:1 to about 20:1. In the context of a fabric laundry composition, usage levels may also vary depending not only on the type and severity of the soils and stains, but also on the wash water temperature, the volume of wash water, and the type of washing machine (e.g., top-loading, front-loading, top-loading, vertical-axis Japanese-type or to about 10° C. The fabric may be contacted to the water prior to, or after, or simultaneous with, contacting the laundry cleaning composition with water.

Another method includes contacting a nonwoven substrate impregnated with an embodiment of the cleaning composition with soiled material. As used herein, "nonwoven substrate" can comprise any conventionally fashioned nonwoven sheet or web having suitable basis weight, caliper (thickness), absorbency, and strength characteristics. Non-limiting examples of suitable commercially available nonwoven substrates include those marketed under the tradenames SONTARA® by DuPont and POLYWEB® by James River Corp. automatic washing machine).

The cleaning compositions herein may be used for laundering of fabrics at reduced wash temperatures. These methods of laundering fabric comprise the steps of delivering a laundry cleaning composition to water to form a wash liquor and adding a laundering fabric to said wash liquor, wherein the wash liquor has a temperature of above 0° C. to about 20° C., or to about 15° C.

Hand washing methods, and combined handwashing with semiautomatic washing machines, are also included.

Machine Dishwashing Methods

Methods for machine-dishwashing or hand dishwashing soiled dishes, tableware, silverware, or other kitchenware, are included. One method for machine dishwashing comprises treating soiled dishes, tableware, silverware, or other kitchenware with an aqueous liquid having dissolved or dispensed therein an effective amount of a machine dishwashing composition in accord with the invention. By an effective amount of the machine dishwashing composition it is meant from about 8 g to about 60 g of product dissolved or dispersed in a wash solution of volume from about 3 L to about 10 L.

One method for hand dishwashing comprises dissolution of the cleaning composition into a receptacle containing water, followed by contacting soiled dishes, tableware, silverware, or other kitchenware with the dishwashing liquor, then hand scrubbing, wiping, or rinsing the soiled dishes, tableware, silverware, or other kitchenware. Another method for hand dishwashing comprises direct application of the cleaning composition onto soiled dishes, tableware, silverware, or other kitchenware, then hand scrubbing, wiping, or rinsing the soiled dishes, tableware, silverware, or other kitchenware. In some examples, an effective amount of cleaning composition for hand dishwashing is from about 0.5 ml. to about 20 ml. diluted in water.

Packaging for the Compositions

The cleaning compositions described herein can be packaged in any suitable container including those constructed from paper, cardboard, plastic materials, and any suitable laminates. An optional packaging type is described in European Application No. 94921505.7.

Multi-Compartment Pouch Additive

The cleaning compositions described herein may also be packaged as a multi-compartment cleaning composition.

SYNTHESIS EXAMPLES

Example 1

1 mol 1,2-pentanediol+3.4 mol propylene oxide, Aminated 1a) 1 mol 1,2-pentanediol+3.4 mol propylene oxide In a 2 l autoclave 208.3 g 1,2-pentanediol and 6.03 g potassium hydroxide (50% in water) were mixed and stirred under vacuum (<10 mbar) at 120° C. for 2 h. The autoclave was purged with nitrogen and heated to 140° C. 394.2 g propylene oxide was added in portions within 5 h. To complete the reaction, the mixture was allowed to post-react for additional 5 h at 140° C. The reaction mixture was stripped with nitrogen and volatile compounds were removed in vacuo at 80° C. Potassium hydroxide was removed by adding 18.1 g synthetic magnesium silicate (Macrosorb MP5plus, Ineos Silicas Ltd.). The mixture was stirred for 2 h at 90° C. and <10 mbar. After filtration 605.5 g of a light yellowish oil was obtained (hydroxy value: 336.3 mgKOH/g).

1b) 1 mol 1,2-pentanediol+3.4 mol propylene oxide, Aminated

In a 9 l autoclave 500.0 g of the resulting alkoxylated dialcohol from example 1-a, 1200 mL of THF and 1500.0 g of ammonia were mixed in the presence of 500 mL of a solid catalyst. The catalyst containing oxides of nickel, copper and molybdenum on zirconium dioxide was in the form of 3×3 mm tablets. The autoclave was purged with hydrogen and pressurized to 20 bar before the mixture was heated to 205° C. The pressure was increased to 280 bar and the reaction mixture was stirred for 15 hours at 205° C. and the total pressure was maintained at 280 bar. After 15 hours the autoclave was cooled to ambient temperature, the product was collected, filtered, and stripped on a rotary evaporator to remove light amines and water. A total of 450.0 g of a low-color etheramine mixture was isolated. The analytical results thereof are shown in Table 1.

TABLE 1

| Total amine-value mg KOH/g | Total acetylata-bles mg KOH/g | Secondary and tertiary amine value mg KOH/g | Tertiary amine-value mg KOH/g | Hy-droxyl value mg KOH/g | Grade of amina-tion in % | Primary Amine in % of total amine |
|---|---|---|---|---|---|---|
| 372.40 | 379.50 | 5.87 | 0.43 | 7.53 | 98.02 | 98.42 |

Example 2

1 mol 1,2-hexanediol+3.4 mol propylene oxide, Aminated 2a) 1 mol 1,2-hexanediol+3.4 mol propylene oxide In a 2 l autoclave 236.3 g 1,2-hexanediol and 6.3 g potassium hydroxide (50% in water) were mixed and stirred under vacuum (<10 mbar) at 120° C. for 2 h. The autoclave was purged with nitrogen and heated to 140° C. 394.2 g propylene oxide was added in portions within 5 h. To complete the reaction, the mixture was allowed to post-react for additional 5 h at 140° C. The reaction mixture was stripped with nitrogen and volatile compounds were removed in vacuo at 80° C. Potassium hydroxide was removed by adding 19.0 g synthetic magnesium silicate (Macrosorb MP5plus, Ineos Silicas Ltd.). The mixture was stirred for 2 h at 90° C. and <10 mbar. After filtration 631.0 g of a light yellowish oil was obtained (hydroxy value: 315.4 mgKOH/g).

2b) 1 mol 1,2-hexanediol+3.4 mol propylene oxide, Aminated

In a 9 l autoclave 500.0 g of the resulting alkoxylated dialcohol from example 2-a, 1200 mL of THF and 1500.0 g of ammonia were mixed in the presence of 200 mL of a solid catalyst. The catalyst containing oxides of nickel, copper and molybdenum on zirconium dioxide was in the form of 3×3 mm tablets. The autoclave was purged with hydrogen and pressurized to 20 bar before the mixture was heated to 205° C. The pressure was increased to 280 bar and the reaction mixture was stirred for 15 hours at 205° C. and the total pressure was maintained at 280 bar. After 15 hours the autoclave was cooled to ambient temperature, the product was collected, filtered, and stripped on a rotary evaporator to remove light amines and water. A total of 450.0 g of a low-color etheramine mixture was isolated. The analytical results thereof are shown in Table 2.

TABLE 2

| Total amine-value mg KOH/g | Total acetylata-bles mg KOH/g | Secondary and tertiary amine value mg KOH/g | Tertiary amine-value mg KOH/g | Hy-droxyl value mg KOH/g | Grade of amina-tion in % | Primary Amine in % of total amine |
|---|---|---|---|---|---|---|
| 350.40 | 357.50 | 7.03 | 1.85 | 8.95 | 97.51 | 97.99 |

Example 3

1 mol 1,2-octanediol+3.4 mol propylene oxide, Aminated 3a) 1 mol 1,2-octanediol+3.4 mol propylene oxide In a 2 l autoclave 248.6 g 1,2-octanediol and 5.8 g potassium hydroxide (50% in water) were mixed and stirred under vacuum (<10 mbar) at 120° C. for 2 h. The autoclave was purged with nitrogen and heated to 140° C. 335.2 g Propylene oxide was added in portions within 5 h. To complete the reaction, the mixture was allowed to post-react for additional 5 h at 140° C. The reaction mixture was stripped with nitrogen and volatile compounds were removed in vacuo at 80° C. Potassium hydroxide was removed by adding 17.5 g synthetic magnesium silicate (Macrosorb MP5plus, Ineos Silicas Ltd.). The mixture was stirred for 2 h at 90° C. and <10 mbar. After filtration 585.0 g of a yellowish oil was obtained (hydroxy value: 293.2 mgKOH/g).

3b) 1 mol 1,2-octanediol+3.4 mol propylene oxide, Aminated

In a 9 l autoclave 500 mL of the resulting alkoxylated dialcohol from example 3-a, 1200 mL of THF and 1500.0 g of ammonia were mixed in the presence of 200 mL of a solid catalyst. The catalyst containing oxides of nickel, copper and molybdenum on zirconium dioxide was in the form of 3×3 mm tablets. The autoclave was purged with hydrogen and pressurized to 20 bar before the mixture was heated to 205° C. The pressure was increased to 280 bar and the reaction mixture was stirred for 15 hours at 205° C. and the total pressure was maintained at 280 bar. After 15 hours the autoclave was cooled to ambient temperature, the product was collected, filtered, and stripped on a rotary evaporator to remove light amines and water. A total of 450.0 g of a low-color etheramine mixture was isolated. The analytical results thereof are shown in Table 3.

TABLE 3

| Total amine-value mg KOH/g | Total acetylatables mg KOH/g | Secondary and tertiary amine value mg KOH/g | Tertiary amine-value mg KOH/g | Hydroxyl value mg KOH/g | Grade of amination in % | Primary Amine in % of total amine |
|---|---|---|---|---|---|---|
| 299.20 | 308.40 | 6.68 | 1.19 | 10.39 | 96.64 | 97.77 |

Example 4

1 mol 1,2-decanediol+3.4 mol propylene oxide, Aminated

4a) 1 mol 1,2-decanediol+3.4 mol propylene oxide

In a 2 l autoclave 278.8 g 1,2-decanediol and 5.9 g potassium hydroxide (50% in water) were mixed and stirred under vacuum (<10 mbar) at 120° C. for 2 h. The autoclave was purged with nitrogen and heated to 140° C. 315.5 g Propylene oxide was added in portions within 5 h. To complete the reaction, the mixture was allowed to post-react for additional 5 h at 140° C. The reaction mixture was stripped with nitrogen and volatile compounds were removed in vacuo at 80° C. Potassium hydroxide was removed by adding 18.0 g synthetic magnesium silicate (Macrosorb MP5plus, Ineos Silicas Ltd.). The mixture was stirred for 2 h at 90° C. and <10 mbar. After filtration 595.0 g of a yellow oil was obtained (hydroxy value: 278.4 mgKOH/g).

4b) 1 mol 1,2-decanediol+3.4 mol propylene oxide, Aminated

In a 9 l autoclave 500 mL of the resulting alkoxylated dialcohol from example 4-a, 1200 mL of THF and 1500 g of ammonia were mixed in the presence of 200 mL of a solid catalyst. The catalyst containing oxides of nickel, copper and molybdenum on zirconium dioxide was in the form of 3×3 mm tablets. The autoclave was purged with hydrogen and pressurized to 20 bar before the mixture was heated to 205° C. The pressure was increased to 280 bar and the reaction mixture was stirred for 15 hours at 205° C. and the total pressure was maintained at 280 bar. After 15 hours the autoclave was cooled to ambient temperature, the product was collected, filtered, and stripped on a rotary evaporator to remove light amines and water. A total of 400 g of a low-color etheramine mixture was isolated. The analytical results thereof are shown in Table 4.

TABLE 4

| Total amine-value mg KOH/g | Total acetylatables mg KOH/g | Secondary and tertiary amine value mg KOH/g | Tertiary amine-value mg KOH/g | Hydroxyl value mg KOH/g | Grade of amination in % | Primary Amine in % of total amine |
|---|---|---|---|---|---|---|
| 319.15 | 328.00 | 6.90 | 0.73 | 9.58 | 97.09 | 97.84 |

Example 5

1 mol 1,2-dodecanediol+3.4 mol propylene oxide, Aminated

5a) 1 mol 1,2-dodecanediol+3.4 mol propylene oxide

In a 2 l autoclave 337.2 g 1,2-dodecanediol and 6.0 g potassium hydroxide (50% in water) were mixed and stirred under vacuum (<10 mbar) at 120° C. for 2 h. The autoclave was purged with nitrogen and heated to 140° C. 295.8 g Propylene oxide was added in portions within 5 h. To complete the reaction, the mixture was allowed to post-react for additional 5 h at 140° C. The reaction mixture was stripped with nitrogen and volatile compounds were removed in vacuo at 80° C. Potassium hydroxide was removed by adding 19.1 g synthetic magnesium silicate (Macrosorb MP5plus, Ineos Silicas Ltd.). The mixture was stirred for 2 h at 90° C. and <10 mbar. After filtration 636.0 g of a yellow oil was obtained (hydroxy value: 275.5 mgKOH/g).

5b) 1 mol 1,2-dodecanediol+3.4 mol propylene oxide, Aminated

In a 9 l autoclave 500 g of the resulting alkoxylated dialcohol from example 5-a, 1200 mL of THF and 1500 g of ammonia were mixed in the presence of 200 mL of a solid catalyst. The catalyst containing oxides of nickel, copper and molybdenum on zirconium dioxide was in the form of 3×3 mm tablets. The autoclave was purged with hydrogen and pressurized to 20 bar before the mixture was heated to 205° C. The pressure was increased to 280 bar and the reaction mixture was stirred for 15 hours at 205° C. and the total pressure was maintained at 280 bar. After 15 hours the autoclave was cooled to ambient temperature, the product was collected, filtered, and stripped on a rotary evaporator to remove light amines and water. A total of 450.0 g of a low-color etheramine mixture was isolated. The analytical results thereof are shown in Table 5

TABLE 5

| Total amine-value mg KOH/g | Total acetylatables mg KOH/g | Secondary and tertiary amine value mg KOH/g | Tertiary amine-value mg KOH/g | Hydroxyl value mg KOH/g | Grade of amination in % | Primary Amine in % of total amine |
|---|---|---|---|---|---|---|
| 282.86 | 289.50 | 5.27 | 2.50 | 9.14 | 96.87 | 98.14 |

Use as Additives in Laundry Detergents

Technical stain swatches of blue knitted cotton containing Beef Fat, Pork Fat, and Bacon Graese were purchased from Warwick Equest Ltd. and washed in conventional western European washing machines (Miele Waschmaschine Softronic W 2241), selecting a 59 min washing cycle without heating and using 75 g of liquid detergent composition LA1 (table 6) together with or without 1.25 g of the etheramine additive and some hydrochloric acid to readjust the pH after addition of the polyetheramine. (pH of 75 g of LA1 in 1 L water should be at pH=8.3). Water hardness was 2.5 mM ($Ca^{2+}:Mg^{2+}$ was 3:1). Standard colorimetric measurement was used to obtain L*, a* and b* values for each stain before and after the washing. From L*, a* and b* values the stain level was calculated.

Stain removal from the swatches was calculated as follows:

$$\text{Stain Removal Index } (SRI) = \frac{\Delta E_{initial} - \Delta E_{washed}}{\Delta E_{initial}} \times 100$$

$\Delta E_{initial}$=Stain level before washing
$\Delta E_{washed}$=Stain level after washing The value of stain removal index increases with better washing performance.

TABLE 6

| liquid detergent composition LA1 | |
|---|---|
| Ingredients of liquid detergent composition LA1 | percentage by weight |
| Alkyl Benzene sulfonate[1] | 7.50% |
| AE3S [2] | 2.60% |
| AE9 [3] | 0.40% |
| NI 45-7 [4] | 4.40% |
| Citric Acid | 3.20% |
| C12-18 Fatty acid | 3.10% |
| Amphiphilic polymer[5] | 0.50% |
| Zwitterionic dispersant[6] | 1.00% |
| Ethoxylated Polyethyleneimine [7] | 1.51% |
| Protease[8] | 0.89% |
| Enymes[9] | 0.21% |
| Chelant[10] | 0.28% |
| Brightener[11] | 0.09% |
| Solvent | 7.35% |
| Sodium Hydroxide | 3.70% |

TABLE 6-continued

| liquid detergent composition LA1 | |
|---|---|
| Ingredients of liquid detergent composition LA1 | percentage by weight |
| Fragrance & Dyes | 1.54% |
| Water, filler, stucturant | To Balance |

[1]Linear alkylbenenesulfonate having an average aliphatic carbon chain length C11-C12 supplied by Stepan, Northfield Illinois, USA
[2] AE3S is C12-15 alkyl ethoxy (3) sulfate supplied by Stepan, Northfield, Illinois, USA
[3] AE9 is C12-14 alcohol ethoxylate, with an average degree of ethoxylation of 9, supplied by Huntsman, Salt Lake City, Utah, USA
[4] NI 45-7 is C14-15 alcohol ethoxylate, with an average degree of ethoxylation of 7, supplied by Huntsman, Salt Lake City, Utah, USA
[5]Amphilic polymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[6]A compound having the following general structure: bis((C2H5O)(C2H4O)n)(CH3)—N+—CxH2x—N+—(CH3)-bis((C2H5O)(C2H4O)n), wherein n = from 20 to 30, and x = from 3 to 8, or sulphated or sulphonated variants thereof
[7] Polyethyleneimine (MW = 600) with 20 ethoxylate groups per —NH
[8]Proteases may be supplied by Genencor International, Palo Alto, California, USA (e.g. Purafect Prime ®)
[9]Natalase ®, is a product of Novozymes, Bagsvaerd, Denmark.
[10]A suitable chelant is diethylene triamine penta(methyl phosphonic) acid supplied by Solutia, St Louis, Missouri, USA;
[11]Fluorescent Brightener 1 is Tinopal ® AMS, Fluorescent Brightener 2 supplied by Ciba Specialty Chemicals, Basel, Switzerland

TABLE 7

| Wash Results: | | | | | |
|---|---|---|---|---|---|
| Stain | A | B | C | D | E |
| Beef Fat | 61.1 | 63.4 | 67.8 | 69.5 | 69.9 |
| Pork Fat | 58.5 | 61.2 | 67.6 | 71.3 | 71.2 |
| Bacon Grease | 62.4 | 64.9 | 71.2 | 73.3 | 73.7 |

A: liquid detergent composition LA1 (see Table 6) without additional etheramine additive
B: liquid detergent composition LA1 (see Table 6) with 1.25 g polyetheramine (2-Aminomethylethyl)-omega-(2-aminomethylethoxy)-poly(oxy(methyl-1,2-ethandiyl)), sold under the trade name Polyetheramine ® D 230 or JEFFAMINE ® D-230 (Comparative example)
C: liquid detergent composition LA1 (see Table 6) with 1.25 g of the etheramine described in Example 1
D: liquid detergent composition LA1 (see Table 6) with 1.25 g of the etheramine described in Example 2
E: liquid detergent composition LA1 (see Table 2) with 1.25 g of the etheramine described in Example 3

The invention claimed is:
1. A composition comprising etheramines of formula (I) and formula (II),

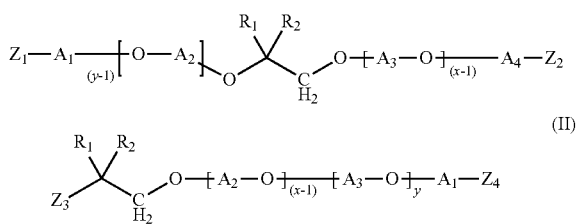

wherein
$R_1$ is a linear or branched alkyl group with 2 to 16 carbon atoms,
$R_2$ is a hydrogen or an alkyl group with 1 to 16 carbon atoms,
$x \geq 1$ and $y \geq 1$ and the sum of x+y is between 2 and 10, and
$A_1$, $A_2$, $A_3$ and $A_4$ are independently selected from the group consisting of linear and/or branched alkylenes having 2 to 18 carbon atoms,
wherein $Z_1$-$Z_4$ are independently selected from OH, $NH_2$, NHR' or NR'R", wherein at least one of $Z_1$ or $Z_2$ and at least one of $Z_3$ or $Z_4$ is $NH_2$, NHR' or NR'R", wherein R' and R" are independently selected from alkylenes having 2 to 6 carbon atoms.

2. The composition according to claim 1, wherein $A_1$, $A_2$, $A_3$ and $A_4$ are independently selected from 1,2-propylene or 1,2-butylene.

3. The composition according to claim 1, wherein $A_1$, $A_2$, $A_3$ and $A_4$ are each 1,2-propylene.

4. The composition according to claim 1, wherein x+y is in the range of from 3 to 6.

5. The composition according to claim 1, wherein $R_1$ is a linear or branched alkyl group with 3 to 16 carbon atoms and $R_2$ is hydrogen or an alkyl group with 1 to 16 carbon atoms.

6. The composition according to claim 1, wherein $R_1$ is a linear alkyl group with 3 to 8 carbon atoms and $R_2$ is hydrogen.

7. The composition according to claim 1, wherein $Z_1$ to $Z_4$ are each $NH_2$.

8. The composition according to claim 1, wherein the etheramine of formula (I) and formula (II) has a weight average molecular weight of from about 270 to about 1000 grams/mole.

9. The composition according to claim 1, wherein the etheramines of formula (I) and formula (II) are reacted with an acid.

10. A process for the manufacture of a composition comprising etheramines of formula (I) and formula (II) according to claim 1 comprising the following steps:
alkoxylation of a 1,2-dialcohol of formula (III) with $C_2$-$C_{18}$ alkylene oxides, wherein the molar ratio of the 1,2-dialcohol of formula (III) to $C_2$-$C_{18}$ alkylene oxides is in the range of 1:2 to 1:10,

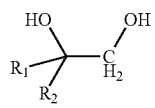
(III)

wherein $R_1$ is a linear or branched alkyl group with 3 to 16 carbon atoms and $R_2$ is a hydrogen or an alkyl group with 1 to 16 carbon atoms,
amination of the alkoxylated 1,2-dialcohol with ammonia.

11. The process according to claim 10, wherein the molar ratio of 1,2-dialcohol to $C_2$-$C_{18}$ alkylene oxides is in the range of 1:3 to 1:8.

12. The process according to claim 10, wherein the molar ratio of 1,2-dialcohol to $C_2$-$C_{18}$ alkylene oxides is in the range of 1:4 to 1:6.

13. The process according to claim 10, wherein the $C_2$-$C_{18}$ alkylene oxides are selected from propylene oxide, butylene oxide or a mixture thereof.

14. The process according to claim 10, wherein the $C_2$-$C_{18}$ alkylene oxide is propylene oxide.

15. The process according to claim 10, wherein the 1,2-dialcohol of formula (III) is selected from the group consisting of 1,2-pentanediol, 1,2-hexanediol, 1,2-heptanediol, 1,2-octanediol, 1,2-nonanediol, 1,2-decanediol, 1,2-dodecanediol, 1,2-tetradecandiol, 1,2 hexadecandiol and 1,2 octadecandiol.

16. The process according to claim 10, wherein the amination is carried out in the presence of a catalyst that comprises at least one of copper, nickel or cobalt.

17. The process according to claim 16, wherein the catalyst, before the reduction thereof with hydrogen, comprises oxygen compounds of aluminum, of copper, of nickel and of cobalt, and in the range from 0.2 to 5.0% by weight of oxygen compounds of tin, calculated as SnO.

18. A personal care product comprising the composition of claim 1.

19. The personal care product of claim 18 selected from a shampoo or a body wash formulation.

20. A curing agent for epoxy resins comprising the composition of claim 1.

21. A polymer selected from a polyurethane, a polyurea, or a thermoplastic polyamide adhesive comprising the composition of claim 1.

22. A composition comprising etheramines of formula (I) and formula (II),

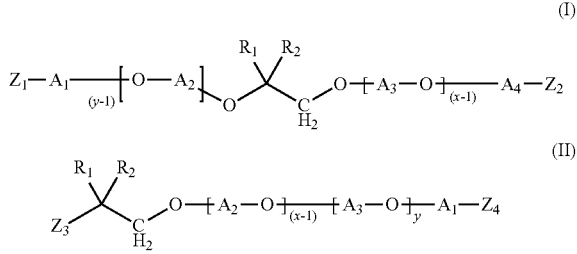

wherein
$R_1$ is a linear or branched alkyl group with 2 to 16 carbon atoms,
$R_2$ is a hydrogen or an alkyl group with 1 to 16 carbon atoms,
$x \geq 1$ and $y \geq 1$ and the sum of x+y is between 2 and 10, and
$A_1$, $A_2$, $A_3$ and $A_4$ are independently selected from 1,2-propylene or 1,2-butylene, and at least one of $A_1$, $A_2$, $A_3$ or $A_4$ is 1,2-propylene,
wherein $Z_1$ to $Z_4$ are independently selected from OH, $NH_2$, NHR' or NR'R", wherein at least one of $Z_1$ or $Z_2$ and at least one of $Z_3$ or $Z_4$ is $NH_2$, NHR' or NR'R", wherein R' and R" are independently selected from alkylenes having 2 to 6 carbon atoms.

23. The composition according to claim 22, wherein $A_1$, $A_2$, $A_3$ and $A_4$ are each 1,2-propylene, and x+y is in the range of from 3 to 6.

24. The composition according to claim 23, wherein $R_1$ is a linear alkyl group with 3 to 8 carbon atoms, $R_2$ is hydrogen, and $Z_1$ to $Z_4$ are each $NH_2$.

* * * * *